(12) United States Patent
Azevedo Pina Vaz et al.

(10) Patent No.: US 11,485,993 B2
(45) Date of Patent: Nov. 1, 2022

(54) THERAPEUTIC DRUG MONITORING

(71) Applicant: Fastinov S.A., Leca Da Palmeira (PT)

(72) Inventors: Cidalia Irene Azevedo Pina Vaz, Leca Da Palmeira (PT); Acacio Agostinho Goncalves Rodrigues, Leca Da Palmeira (PT)

(73) Assignee: Fastinov S.A., Leca Da Palmeira (PT)

( * ) Notice: Subject to any disclaimer, the term of this patent is extended or adjusted under 35 U.S.C. 154(b) by 400 days.

(21) Appl. No.: 16/617,817

(22) PCT Filed: Jun. 1, 2018

(86) PCT No.: PCT/PT2018/050021
§ 371 (c)(1),
(2) Date: Nov. 27, 2019

(87) PCT Pub. No.: WO2018/222061
PCT Pub. Date: Dec. 6, 2018

(65) Prior Publication Data
US 2020/0190554 A1 Jun. 18, 2020

Related U.S. Application Data

(60) Provisional application No. 62/514,323, filed on Jun. 2, 2017.

(51) Int. Cl.
*C12Q 1/18* (2006.01)
*G01N 15/14* (2006.01)
*G01N 15/10* (2006.01)

(52) U.S. Cl.
CPC .......... *C12Q 1/18* (2013.01); *G01N 15/1456* (2013.01); *G01N 2015/1006* (2013.01)

(58) Field of Classification Search
None
See application file for complete search history.

(56) References Cited

U.S. PATENT DOCUMENTS

| | | | |
|---|---|---|---|
| 6,867,015 | B1 | 3/2005 | Langeveld et al. |
| 8,609,364 | B2 | 12/2013 | Walsh et al. |
| 9,290,790 | B2 | 3/2016 | Azevedo Pina Vaz et al. |
| 2009/0068696 | A1 | 3/2009 | Frimodt-Moller |
| 2015/0056648 | A1 | 2/2015 | Tidwell et al. |

FOREIGN PATENT DOCUMENTS

| | | |
|---|---|---|
| EP | 0 118 274 A1 | 9/1984 |
| EP | 3085790 A1 | 10/2016 |
| JP | 05-038298 A | 2/1993 |
| WO | 1984003303 A1 | 8/1984 |
| WO | 2009095258 A1 | 8/2009 |
| WO | 2012164547 A1 | 6/2012 |
| WO | 2015073589 A1 | 5/2015 |
| WO | 2018203315 A1 | 11/2018 |
| WO | 201822061 A1 | 12/2018 |

OTHER PUBLICATIONS

Barbosa, et al., "A New Method for the Detection of Pneumocystis Jirovecii Using Flow Cytometry", European Journal of Clinical Microbiology & Infectious Diseases, vol. 29, No. 9, pp. 1147-1152, Jun. 16, 2010.
Barbosa, et al., Specific Detection of P. Jiroveci on Clinical Samples by Flow Cytometry, Fungal Diagnostics: Methods and Protocols, vol. 968, pp. 203-211, 2013.
Boardman, et al., "Rapid Microbial Sample Preparation from Blood Using a Novel ConcenliaLion Device", PLoS ONE, vol. 10, No. 2, pp. 1-13, Feb. 12, 2015.
Bownds, et al., "Rapid Susceptibility Testing for Nontuberculosis Mycobacteria Using Flow Cytometry," Journal of Clinical Mcrobiology, vol. 34, No. 6, pp. 1386-1390, Jun. 1996.
Budikhina, et al., "Evaluation of Bactericidal Activity of Human Biological Fluids by Flow Cytofluorimetry," Immune Advances in Experimental Medicine and Biology, vol. 601, pp. 307-310, 2007.
Carlier, et al., "Assays for Therapeutics Drug Monitoring of [Beta]-Lactam Antibiotics: A Structured Review," International Journal of Antimicrobial Agents, vol. 46, Issue No. 4, pp. 367-375, Oct. 1, 2015.
Costa-de-Oliveira, et al., "Clinical and Economical Impact of a Rapid Susceptibility Testing Regarding Blood Cultures with Gram Negative Bacilli", 26 ECCMID, Amsterdam, Netherlands, Apr. 2016.
Espinar, et al., "Rapid Detection of Extended-Spectrum B-Lactamase Producing Bacteria by Means of Flow Cytometry", Clinical Microbiology & Infection, vol. 16, Apr. 2010.
Lee, et al., "Antifungal Susceptibility Testing of *Candida* Species by Flow Cytometry", J. Korean Med. Sci. Vol. 14, pp. 21-26, Feb. 1, 1999.
O'Brien-Simpson, et al., "A Rapid and Quantitative Flow Cytometry Method for the Analysis of Membrane Disruptive Antimicrobial Activity," PLoS ONE, p. e151694, Mar. 17, 2016.
Pina-Vaz et al., "Susceptibility to Fluconazole of Candida Clinical Isolates Determined by FUN-1 Staining with Flow Cytometry and Epifluorescence Microscopy", J. Med. Microbiology, vol. 50, pp. 375-382, Apr. 1, 2001.
Pina-Vaz et al., "Cytometric Approach for a Rapid Evaluation of Susceptibility of Candida Strains to Antifungals", Clinical Microbiology and Infection, vol. 7, Issue 11, pp. 609-618, Nov. 1, 2001.

(Continued)

*Primary Examiner* — Robert J Yamasaki
(74) *Attorney, Agent, or Firm* — Greenberg Traurig, LLP; David J. Dykeman; Fang Xie

(57) ABSTRACT

Disclosed herein are methods and compositions for antimicrobial quantification and functional measurement. In one aspect, a method for quantifying antimicrobial comprises: obtaining a biological sample from a patient receiving an antimicrobial; incubating the biological sample with a reference microbial strain and a fluorophore for detecting cell lesion; measuring a first signal of fluorescent intensity in the incubated biological sample using flow cytometry; and comparing the first signal to a calibrating curve previously generated for the antimicrobial, thereby quantifying the antimicrobial present in the biological sample.

9 Claims, 8 Drawing Sheets

(56) References Cited

OTHER PUBLICATIONS

Pina-Vaz et al., "Novel Method Using a Laser Scanning Cytometer for Detection of Mycobacteria in Clinical Samples", Journal of Clinical Microbiology, vol. 42, Issue 2, pp. 906-908, Feb. 1, 2004.
Pina-Vaz et al., "Safe Susceptibility Testing of *Mycobacterium tuberculosis* by Flow Cytometry with the Fluorescent Nucleic Acid Stain SYTO 16", Journal of Medical Microbiology, vol. 4, Issue 1, pp. 77-81, Jan. 1, 2005.
Pina-Vaz et al., "Comparison of Two Probes for Testing Susceptibilities of Pathogenic Yeasts to Voriconazole, Itraconazole, and Caspofungin by Flow Cytometry", Journal of Clinical Microbiology, vol. 43, No. 9, pp. 4674-4679, Sep. 2005.
Pina-Vaz, et al., "Evaluation of Antifungal Susceptibility Using Flow Cytometry", Methods in Molecular Biology, vol. 638, pp. 281-289, Feb. 2010.
Silva et al., "Rapid Flow Cytometry Test for Identification of Different Carbapenemases in Enterobacteriaceae", Antimicrobial Agents and Chemotherapy, vol. 60, No. 6, pp. 3824-3826, Jun. 2016.
Silva, "Rapid antimicrobial susceptibility profile directly from positive blood cultures using flow cytometry" 25th ECCMID, Copenhagen, Denmark—Paper Poster Session VI, 2015.
Singh M., "Rapid Test for Distinguishing Membrane Active Antibacterial Agents", J. of Microbiological Methods, vol. 7, Issue 1, pp. 125-130, Oct. 2006.
Tan J., et al. "Kinetically Limited Differential Centrifugation as an Inexpensive and Readily Available Alternative to Centrifugal Elutriation", BioTechniques, vol. 53, pp. 104-108, Aug. 2012.
Teixeira-Santos et al., A rapid flow cytometry test for detection of vancomycin and linezolid-resistance among Gram-positive bacteria. 23th ECCMID, Bedin, Germany—Abstract (Poster Session), 2013.
Zander, et al., "Piperacillin Concentration in Relation to Therapeutic Range in Critically Ill Patients—A Prospective Observational Study," Critical Care, vol. 20, Issue 79, pp. 1-11, Apr. 4, 2016.
International Search Report in PCT/PT2018/050021 dated Aug. 13, 2018.
Takeda, et al., "Microbiological assay method for cefozopran in biological specimens", Chemotherapy, vol. 41, pp. 135-141, Dec. 1993.

US 11,485,993 B2

THERAPEUTIC DRUG MONITORING

CROSS-REFERENCE TO RELATED APPLICATIONS

This application is a U.S. national phase application of PCT International Patent Application No. PCT/PT2018/050021, filed on Jun. 1, 2018, which claims the benefit of and priority to U.S. Provisional Application No. 62/514,323 filed Jun. 2, 2017, the entire disclosure of each of which is incorporated herein by reference.

FILED OF THE INVENTION

The present disclosure generally relates to methods and compositions for antimicrobial quantification and functional measurement.

BACKGROUND

Prescription of the appropriate type and dosage of antimicrobials (antibiotics and antifungals) to treat severe infections is crucial. Unfortunately, the dosage of antimicrobials does not follow a one-size-fits-all principle, and blood levels of antibiotics in patients receiving the same drug amount can vary up to 100-1000 fold [Zander, J., et al., *Piperacillin concentration in relation to therapeutic range in critically ill patients—a prospective observational study*. Crit Care, 2016. 20: p. 79.]. This high variability is caused by differences in patient characteristics such as renal clearance, liver function, and comorbidities. As a result, blood levels of antimicrobials can either be insufficient to combat an infection, or so high that toxicity develops. To maximize treatment efficacy and minimize adverse side effects, dosage must be adjusted, based upon the measurement of actual blood level of antimicrobials, a process called therapeutic drug monitoring (TDM). Ideally it should follow the in vitro determination of the antimicrobial efficacy to treat the specific infection, that is the antimicrobial susceptibility testing (AST).

TDM is especially valuable for patients in whom pharmacokinetics (PK) and/or pharmacodynamics (PD) may be altered. This is the case most often among critically ill patients suffering from renal or liver insufficiency, those with severe fluid status changes or low albumin levels, or patients receiving renal replacement therapy. Critically ill patients are often affected by severe infections and need prompt and targeted antibiotic treatment. However, due to altered PK/PD profiles the normal dosage regimes are often not sufficient, or may be excessive, e.g., if renal clearance is low, drug excretion is impaired and antibiotics blood levels may become toxic.

Current available TDM methods for antibiotics are based on high-pressure liquid chromatography (HPLC) or immunoassays, both sharing many limitations. Firstly, they are only available for a narrow selection of antibiotics (predominantly aminoglycosides, such as amikacin and gentamicin, and vancomycin). Secondly, these methods are rarely available in clinical microbiology laboratories and are very expensive. And thirdly, these methods, by definition, only deliver data on blood and involve chemical determination, that is, they do not assess the antimicrobial activity, which could be different if for some reason the antibiotic was inactivated in vivo, for instance, by bacterial enzymes or by some other interaction or host factor.

Thus, a need exists for new techniques that can quickly and inexpensively quantify a broad panel of antimicrobials that might be present in a biological sample obtained from a patient receiving antimicrobial treatment, as well as determine its effective antimicrobial activity.

SUMMARY OF THE INVENTION

Disclosed herein are improved methods, compositions and kits for therapeutic drug monitoring (TDM) regarding the most relevant clinical antimicrobial drugs. In some embodiments, flow cytometry can be used. Antimicrobial level of the drugs can be quantified on different body fluids such as blood, urine, cerebrospinal fluid and will quickly allow, e.g., within 2 hours, the establishment of a targeted personalized treatment. This is especially important for critically ill patients with several co-morbidities such as renal and/or hepatic dysfunction.

In one aspect, provided herein is a method for quantifying an antimicrobial in a biological sample, comprising:
  a. obtaining a biological sample from a patient receiving an antimicrobial;
  b. incubating the biological sample with a reference microbial strain and a fluorophore for detecting cell lesion;
  c. measuring a first signal of fluorescent intensity in the incubated biological sample using flow cytometry; and
  d. comparing the first signal to a calibrating curve previously generated for the antimicrobial, thereby quantifying the antimicrobial present in the biological sample.

In some embodiments, the method can further include incubating a separate aliquot of the biological sample with a microbial strain isolated or recovered or derived from the same patient and the fluorophore and measuring a second signal of fluorescence intensity therein using flow cytometry. In certain embodiments, the antimicrobial can be an antibiotic or an antifungal. The biological sample can be one or more of serum, plasma, urine, spinal fluid, ascitic fluid and bronchial secretion or washing. The fluorophore can be selected from DiBAC$_4$ oxonol such as DiBAC$_4$(3) (Bis-(1, 3-Dibutylbarbituric Acid)Trimethine Oxonol), DiOC oxacarbocyanines such as DiOC$_{18}$(3) (3,3'-Dioctadecyloxacarbocyanine Perchlorate), DHR (dihydrorhodamine), propidium iodide, or fluorescein diacetate (FDA) such as C-FDA (5(6)-Carboxyfluorescein diacetate). Other fluorophores known in the art can also be used. In some embodiments, the calibrating curve can be generated using different concentrations of the antimicrobial incubated with the reference microbial strain or with a microbial strain isolated from the same patient under testing.

DETAILED DESCRIPTION

Figure 1:
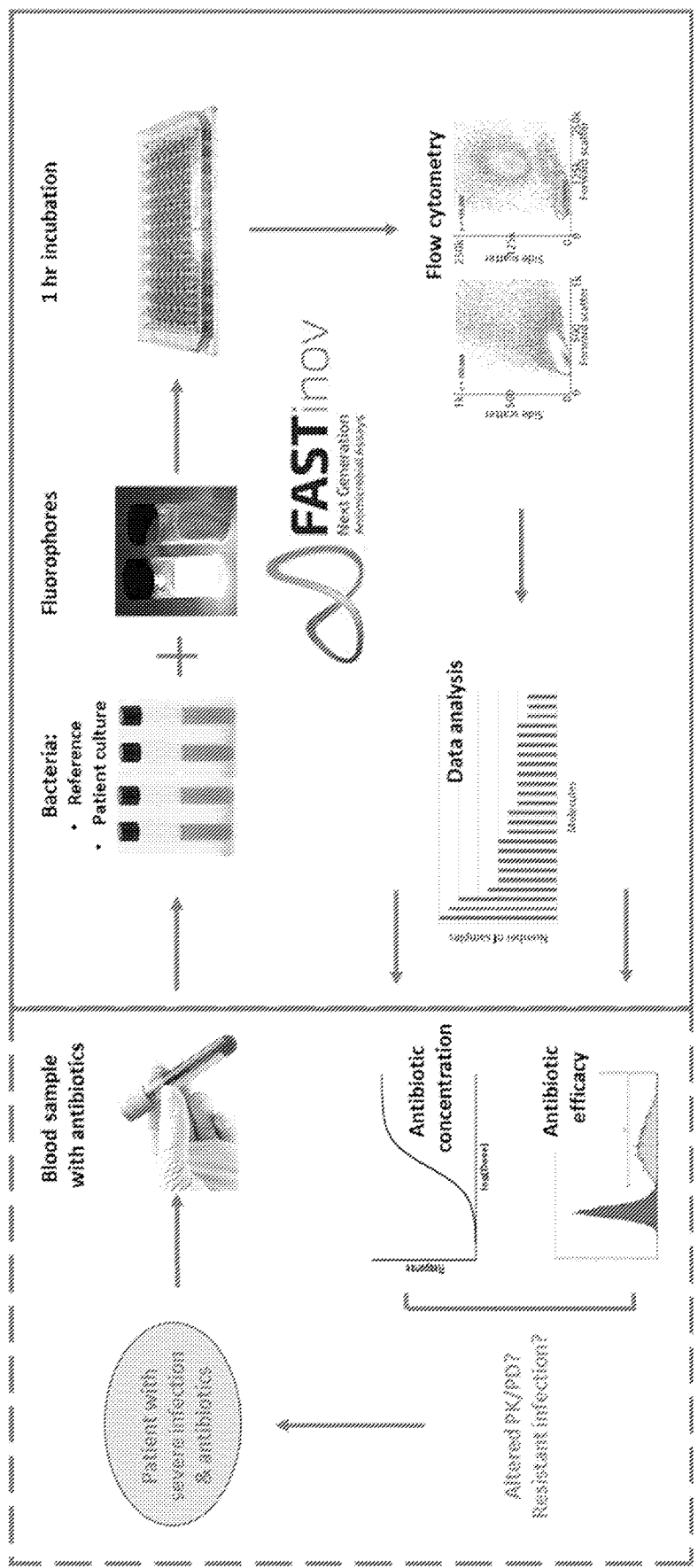
FIG. 1: Diagram showing an exemplary process of the present disclosure for determining antimicrobial concentration and efficacy in a patient receiving the treatment, so as to inform about further treatment strategy.
Figure 2:
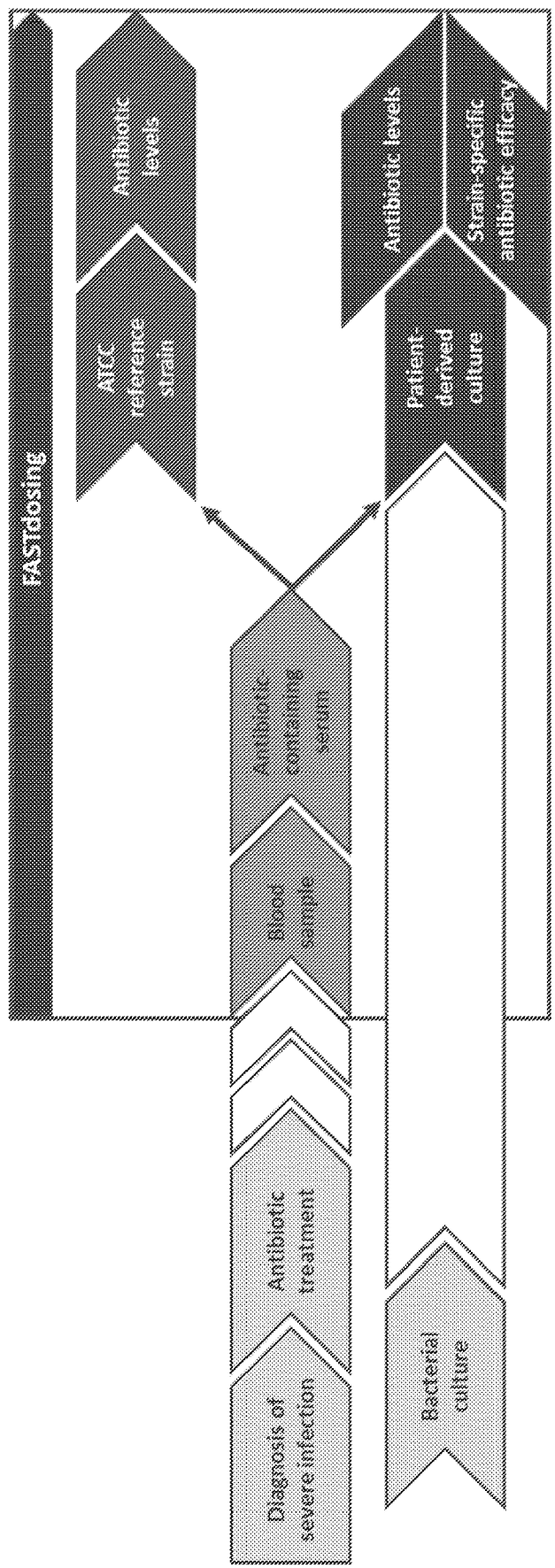
FIG. 2: Flow chart showing an exemplary process of the present disclosure for determining antimicrobial concentration and efficacy in a patient receiving the treatment, so as to inform about further treatment strategy.

Disclosed herein is an improved therapeutic drug monitoring (TDM) assay, as well as related compositions and kits, that measures both antimicrobial levels and its efficacy in biological samples of patients using reference bacterial or fungal strains and/or, whenever available, patient-derived specific bacterial/fungal cultures. The improved TDM dosing assay and kit is based, in some embodiments, upon flow cytometry, and can provide results quickly and accurately, e.g., within 2 hours or less. This is significantly advantageous compared to conventional TDM methods.

In some embodiments, the improved TDM disclosed herein can measure the cellular effects of a panel of antimicrobials (e.g., antibiotics in case of bacteria and/or antifungals in case of fungi), available in a biological sample such as blood or other body fluids. These phenotypical changes can be measured well before the effects on bacterial growth (which is the read-out of conventional methods) become apparent. Phenotypic changes, such as morphofunctional changes, membrane potential, specific membrane lesions or DNA quantity, can be assessed by flow cytometry, and antimicrobial drug efficacy can thus be quickly detected and quantified. These specific changes can be measured using fluorescent probes such as $DiBAC_4$ and DIOC which are membrane-potential sensitive; propidium iodide, a probe that assesses the integrity of the cell membrane; or C-FDA, DHR or FUN-1 to evaluate the metabolic cell status. These probes have been shown to provide a convenient, fast and accurate read-out of the antibiotic effect upon bacteria and fungi.

Following the creation of dose-effect curves (calibrating curves) for each drug, using type reference strains (from American Type Culture Collection (ATCC) for example) and serial antimicrobial concentrations, the desirable approach can be used for standardized drug concentration measurement. Essentially, the effect of the unknown concentration of specific antimicrobial in the serum sample (or other body fluid sample) obtained from the patient can be compared with the corresponding calibration curve, thus providing a fast and easy method to quantify the effective antimicrobial concentration present in the patient's biological samples. In parallel, the same procedure can be performed with a bacterial or fungal isolate obtained from the same patient, using standard clinical microbiological procedures. Such an approach can be used to establish the effective antimicrobial concentration available in the patient's sample against the patient-specific bacterial or fungal strain, by assessing and quantifying the cell lesion exhibited by such strain.

In certain embodiments, various biological samples can be collected from infected patients, such as blood from blood cultures, spinal, pericardial, pleural or peritoneal fluid, urine, bronchial secretions or bronchial washing. Antimicrobial treatment can be initiated later, after Antimicrobial Susceptibility Test (AST). Based on the AST result, the antimicrobial therapy can be initiated. In cases where clinical outcome is not favorable despite the in vitro susceptibility to the drug, especially if the patient exhibits renal or hepatic dysfunction, serum or other liquid samples can be collected to quantify the amount of effective antimicrobial available at the specific site of infection to determine whether the antimicrobial is present at sufficient level at the site of infection. If not, a different (e.g., increased) amount of antimicrobial or a different antimicrobial can be administered.

The biological sample can be incubated following different dilutions with a type or reference microbial strain and the lesion produced on the microorganism can be quantified by flow cytometry. Following comparison with standard curves the amount of active antimicrobial agent available on the biological sample can be determined.

In case a microbial isolate has been recovered from the same patient, the TDM can be performed with this microbial isolate, instead of a reference strain. Antimicrobial effect obtained in the Antimicrobial Susceptibility Test (AST) in vitro can be compared with the effect of different concentrations of the same antimicrobial in biological samples. This can represent a significant advantage in the selection of therapeutic strategies. For example, if serum level of the antimicrobial is below the assumed therapeutic effective levels (e.g., in patients where therapeutic values are impossible to achieve) but is nevertheless higher than the to minimum inhibitory concentration (MIC) value, the antimicrobial should still be able to cause severe lesion on the microorganism infecting the patient; in that case, therapy does not need to be interrupted or substituted.

The clinician can be informed about the concentration of the antimicrobial prescribed to a patient is above or below the therapeutic intervals, allowing the clinician to make the required adjustments.

This improved TDM method is a microbiological functional method for antimicrobial drug quantification in patient's biological samples. It is a functional assay, which allows the measurement of the activity of the drugs and not only their chemical presence. In addition, as the TDM disclosed herein is based upon a flow cytometric assay and not on the study of the microbe's ability to grow, it is a very fast, reproducible and accurate method. This improved TDM method provides significant advantages over conventional methods, considering the urgent need of an inexpensive, simple and fast method to personalize dosage of antibiotics to treat severe infections. This is due to several reasons:

(1) Blood levels of antibiotics can vary 100-1000 fold between patients when using the same dose;
(2) Critically ill patients, especially those exhibiting altered PK/PD characteristics require fast and personalized treatment;
(3) Dosage can only be personalized if blood levels of antibiotics and their activity are precisely known;

(4) Conventional methods are limited to a few antimicrobials, are very cumbersome and do not measure the antimicrobial activity of the drugs since they only assess chemical presence of the drugs;
(5) Critically ill patients have a far greater chance of being infected with drug-resistant microorganisms which reduces the therapeutic choices and possibilities of a favorable outcome; and
(6) Infection by drug-resistant microorganisms, in particular bacteria and fungi represents a growing threat in Europe and USA, making the need for personalized dosing especially urgent and mandatory.

In addition, the methods and compositions disclosed herein can also be used in other applications such as:
(1) Antimicrobial dosing in water for environmental monitoring/bioremediation purposes;
(2) Quality control of antimicrobial drugs, such us variation between different providers and/or different lots;
(3) Antimicrobial monitoring of banned drugs, in order to ensure food safety; application in raw food (meat, plant) extracts or animal body fluids;
(4) In veterinary medicine, with the same purposes as above described in clinical medicine for humans.

EXAMPLES

Additional features of the present disclosure are described in the following non-limiting Examples. It is to be understood, however, that these examples are included solely for the purpose of exemplifying aspects of the present disclosure. They should not be understood in any way as a restriction of the broad description of the disclosure as set out above.

Example 1: Quantification and Measurement of the Antimicrobial Activity of Colistin Colistin is increasingly being prescribed as a rescue treatment for infections with multidrug-resistant bacilli. Colistin is an old antimicrobial but, is at present, the only alternative against superbug strains like those producing carbapenemases, and multi-resistant *Pseudomonas aeruginosa* and *Acinetobacter baumannii*. Since its pharmacokinetics is not yet well known, it would be very useful to have the possibility to measure its antibacterial activity in each individual patient receiving it. Often, nephrotoxicity and, to a lesser degree, neurotoxicity can occur during systemic colistin therapy; such adverse side effects have severely limited colistin use in the past. However, these effects are largely reversible and can be managed through close drug monitoring. We have developed a microbiological assay in order to quantify the antimicrobial effect produced by different antimicrobial drugs using flow cytometry, including colistin.

The objective of this example was to optimize the measurement of the antimicrobial activity of colistin in the patient blood using flow cytometry.

Figure 3:
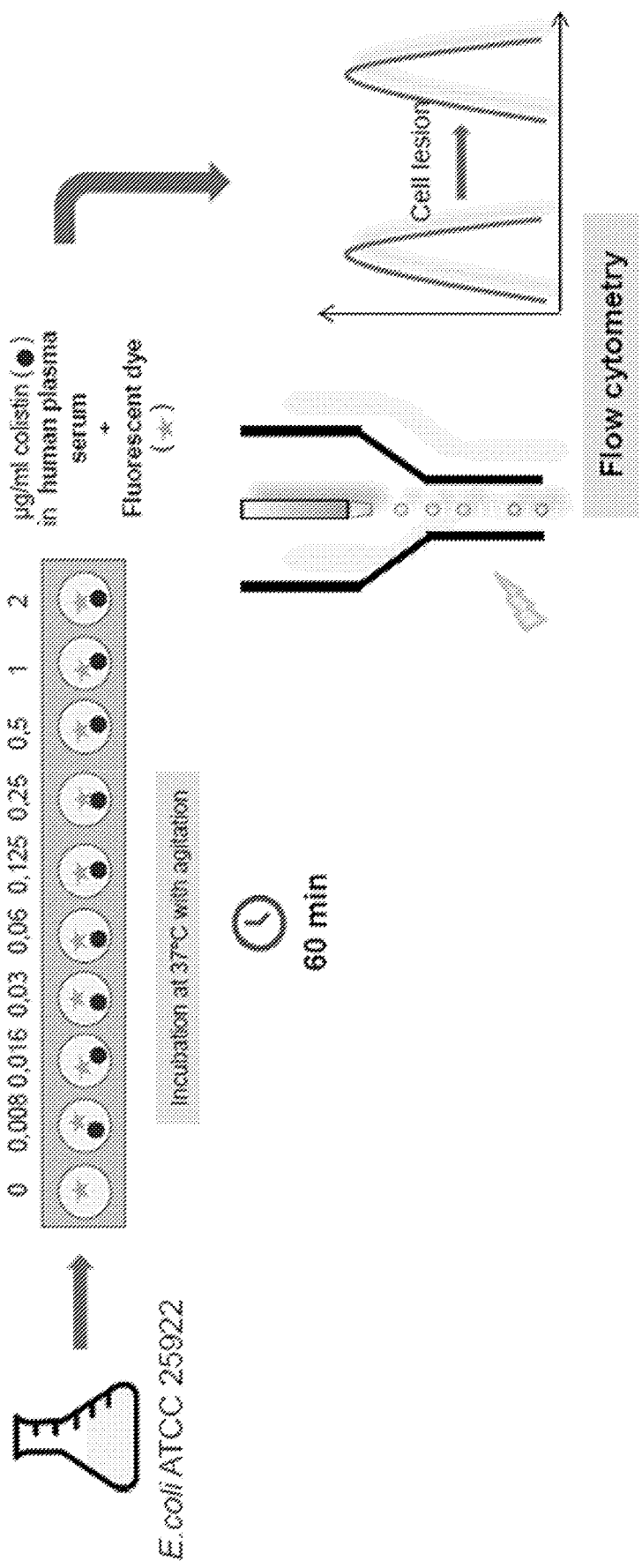
FIG. 3: Exemplary diagram showing the protocol of Example 1.

Serial dilutions of colistin (Sigma), ranging between 0.008 and 2 µg/ml, were inoculated in human plasma (free of colistin) and incubated with *E. coli* ATCC 25922 during 60 minutes and afterwards stained with a fluorescent dye and analyzed in a flow cytometer (Accuri, BD) using a protocol previously optimized (FIG. 3): a flow cytometric template of cell analysis was defined in order to include the majority of the bacterial population and at least 20,000 cells are analyzed according size, complexity and intensity of fluorescence on the different fluorescent channels.

Figure 4:
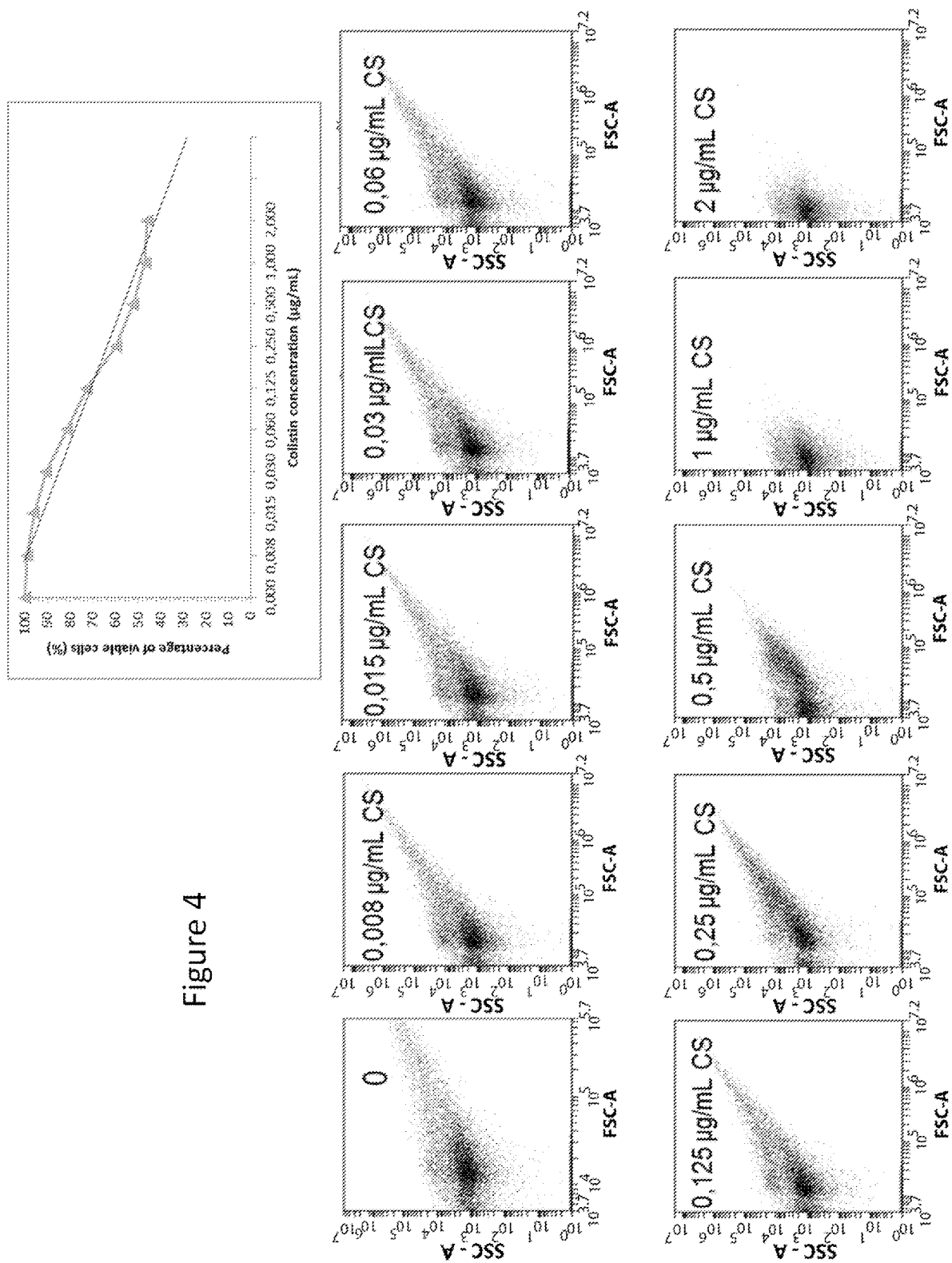
FIG. 4: Graphic representation of the amount of cells at the acquisition gate of the flow cytometer after incubation with increasing concentrations of colistin; a dose-dependent effect was achieved (A). Flow cytometry scattergrams (SSC vs FSC) representing the morphologic changes in bacterial population with the increasing concentrations of colistin; a decrease in the population percentage is evident (B).

Morphological changes were evident on the bacterial cell population following exposure to serial increasing concentrations of colistin (FIG. 4, panel A). Regarding the intensity of fluorescence, a linear effect occurred at concentrations between 0.06 and 1 µg/mL of colistin (FIG. 4, panel B). The effect of higher colistin concentrations could be confirmed after diluting the serum.

Thus, a sensitive and accurate method was developed allowing, in a short time (60 minutes) to quantify the number of colistin impaired cells and conclude about the serum concentration of the active drug. This protocol will be very relevant for critical care patients receiving colistin with low or no clinical improvement. For this assay, a quality control strain or, whenever possible, the own patient isolate could be used for the design of a standard dose-effect curve.

Example 2: Quantification and Measurement of the Antimicrobial Activity of Vancomycin Vancomycin is a glycopeptide antibiotic that has been in clinical use for nearly 50 years as an alternative to penicillin to inhibit penicillinase-producing strains of *Staphylococcus aureus*. Despite limitations such as poor tissue penetration, relatively slow antibacterial effect, and the potential for toxicity, vancomycin is regarded as the gold standard for antibiotic treatment of MRSA infections because of its low cost and established clinical response. Due to the complexity of vancomycin pharmacokinetics and its high toxicity, the monitoring of blood level is recommended in order to obtain therapeutic success. Our research group has been using flow cytometry to evaluate the in vitro susceptibility profile of bacteria with great success, including to vancomycin.

The objective of this work was to optimize the microbiology measurement of the activity of vancomycin in the patient's blood using flow cytometry.

Material and Methods. *S. aureus* ATCC 29213 was incubated for 1 hour with serial concentrations of vancomycin (4 µg/ml to 0.03 µg/ml) in donor drug free human serum and stained with adequate fluorochrome. The intensity of fluorescence and the changes in the scattergram of the bacterial population were recorded after flow cytometry analysis. Twenty samples of serum collected from patients receiving vancomycin were obtained from the biochemistry lab. The vancomycin drug concentrations were analyzed by Architect iVancomycin (Abbott) using the Architect i1000 SR analyzer (Abbott). Architect iVancomycin is an in vitro chemiluminescent microparticle immunoassay (CMIA) for the quantitative measurement of vancomycin in human serum or plasma. In parallel, serum samples were incubated with the *S. aureus* control strain, after 10 serial dilutions (1:2) and analyzed by flow cytometry (Accury, BD) according the protocol described in Example 1. A flow cytometric template of cell analysis was defined in order to include the majority of the bacterial population. A comparison of the concentrations obtained with the Architect iVancomycin method and with the new flow cytometric method was performed using Student's T test.

Figure 5A:
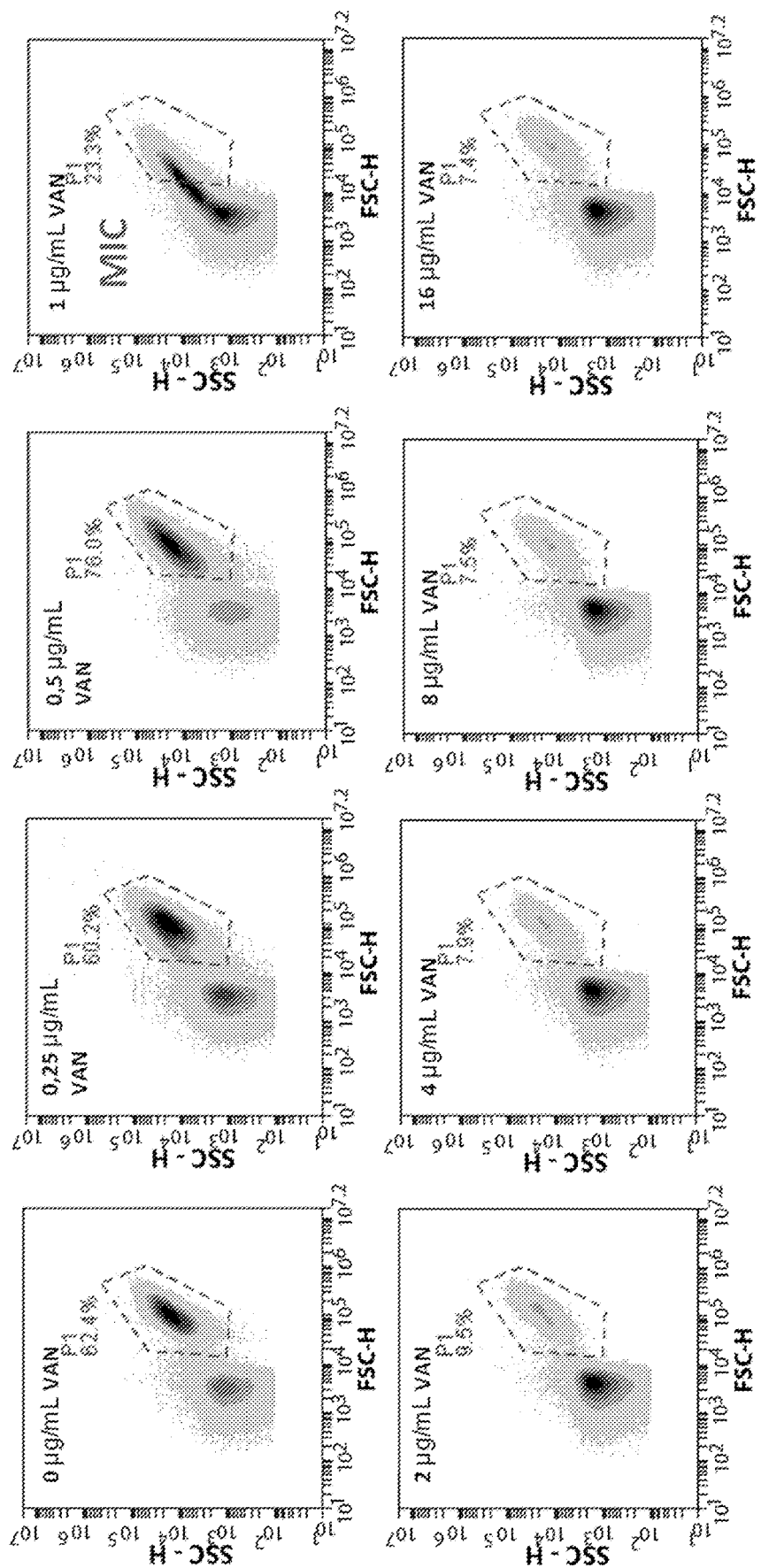
FIG. 5A: Flow cytometry analysis of Flow cytometric TDM using the Flow-cytometry Antimicrobial Susceptibility Test (FAST) dosing kit to determine the dose-dependent effect of vancomycin upon *S. aureus* ATCC 29213 viability, through analysis of cell morphology visualized in scatterplots.
Figure 5B:
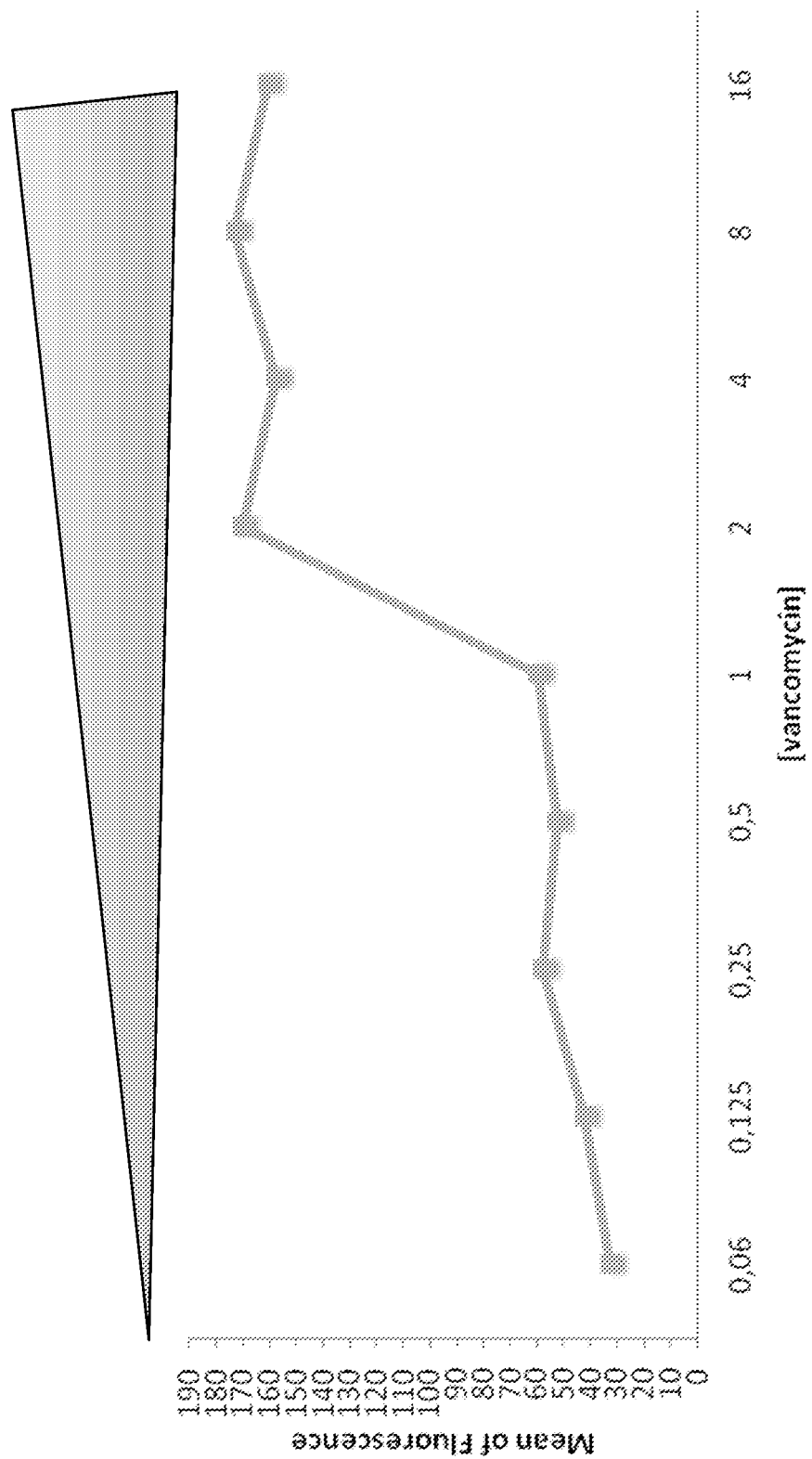
FIG. 5B: Flow cytometry analysis of Flow cytometric TDM using the Flow-cytometry Antimicrobial Susceptibility Test (FAST) dosing kit to determine the dose-dependent effect of vancomycin on *S. aureus* ATCC 29213 viability, through analysis of the intensity of cell fluorescence.

As shown in FIGS. 5A and 5B, following incubation of *S. aureus* (susceptible to low concentrations) with increasing concentration of vancomycin, a dose effect cellular lesion is evident by: the reduction on the cell density plot (percentage of cells on P1, FIG. 5A) and an increase of the intensity of fluorescence (FIG. 5B), both facts indicating cell damage.

Figure 6A:
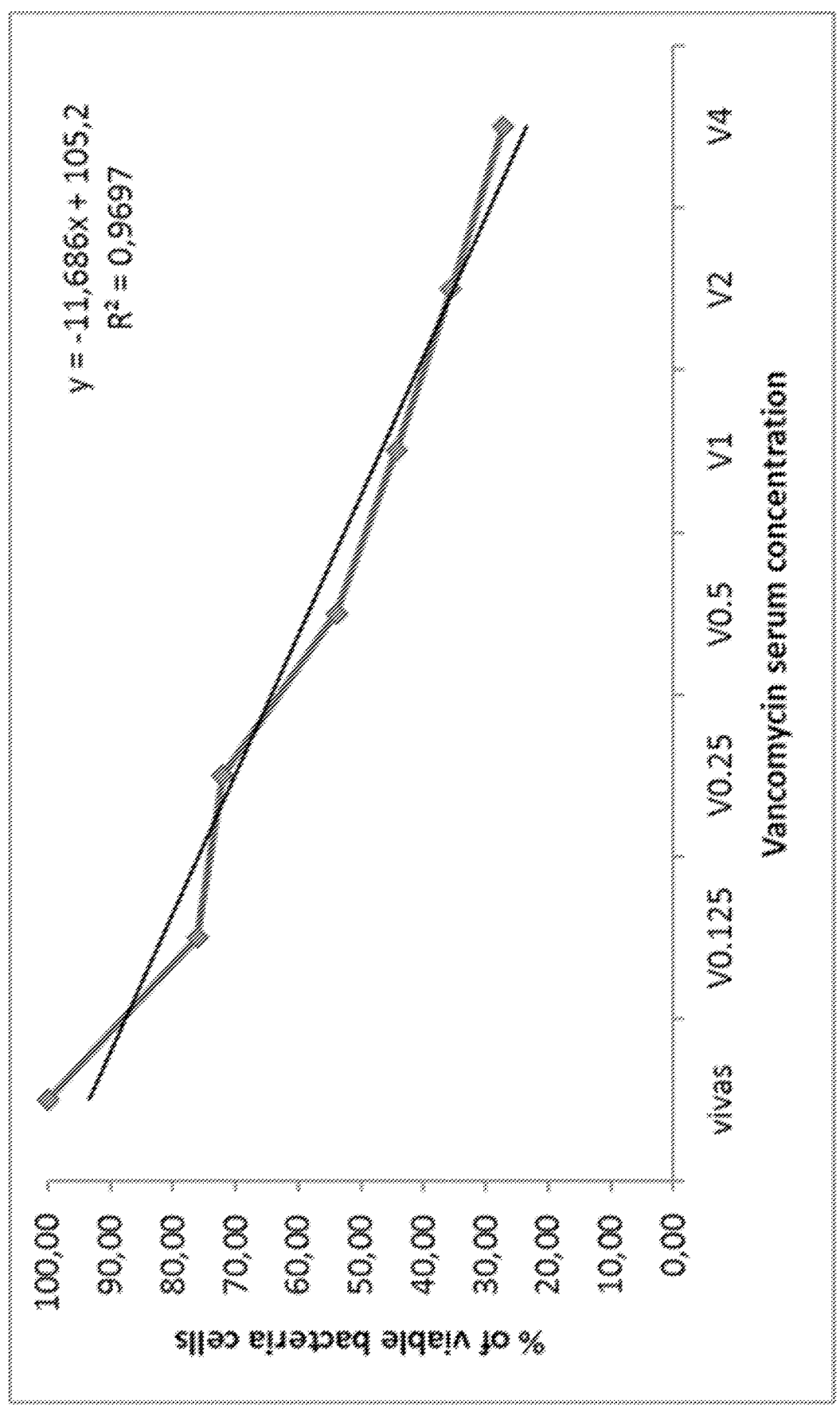
FIG. 6A: Control vancomycin dose curve concentration of *S. aureus* ATCC 29213 strain. The control dose curve effect obtained by flow cytometry showed a linear effect between 0.5 and 4 ug/ml and the coefficient of correlation was calculated.
Figure 6B:
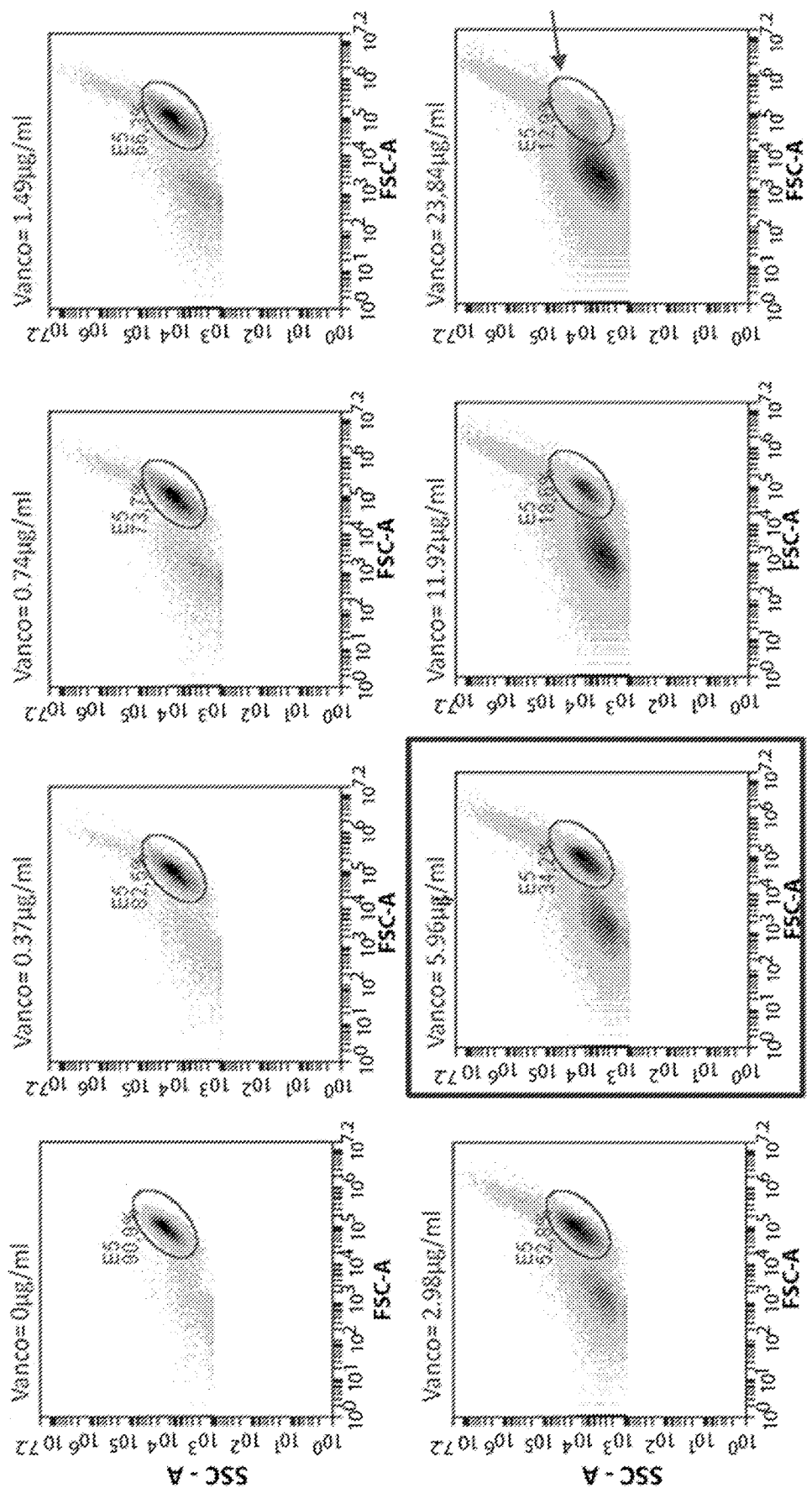
FIG. 6B: Representative example of a flow cytometric scattergram showing a decrease in the bacterial population (red circle) with the concomitant increase of patient vancomycin (vanco) serum concentration.

The control dose curve effect obtained by flow cytometry showed a linear effect between 1 and 0.03 µg/ml and the coefficient of correlation was calculated (FIG. 6A). Patient's serum sample concentration was calculated using linear regression equation obtained from the control curve. Specifically, the concentration of vancomycin in the serum patient sample was determined by using the % of viable cells obtained in FIG. 6B (red square) that was within the linearity range and taking into consideration the serum dilution factor. An excellent correlation between both methods was obtained, with a variation of vancomycin concentration in serum patients of ±5 μg/ml.

Conclusions. A new, simple, convenient and fast method for quantification of vancomycin activity in biological samples was obtained with the advantage of being a fast and functional method reflecting drug antimicrobial activity.

Modifications and variations of the described methods and compositions of the present disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosure are intended and understood by those skilled in the relevant field in which this disclosure resides to be within the scope of the disclosure as represented by the following claims.

All patents and publications mentioned in this specification are herein incorporated by reference to the same extent as if each independent patent and publication was specifically and individually indicated to be incorporated by reference.

The invention claimed is:

1. A method for quantifying an antimicrobial in a biological sample, comprising:
   a. obtaining a biological sample from a patient receiving an antimicrobial;
   b. incubating the biological sample with a reference microbial strain and a fluorophore for detecting microbial cell lesion;
   c. measuring a first signal of fluorescent intensity of the fluorophore in the reference microbial strain in the incubated biological sample using flow cytometry; and
   d. comparing the first signal to a calibrating curve previously generated for the antimicrobial against the reference microbial strain, thereby quantifying the antimicrobial present in the biological sample.

2. The method of claim 1, wherein the biological sample is one or more of serum, plasma, urine, spinal fluid, bronchial secretions or washing or any other body fluid.

3. The method of claim 1, wherein the patient has an infection.

4. The method of claim 1, wherein the antimicrobial is an antibiotic or antifungal.

5. The method of claim 1, wherein the reference microbial strain is an *E. coli* or *S. aureus* strain.

6. The method of claim 1, wherein the fluorophore is selected from $DiBAC_4$, DIOC, propidium iodide, DHR, C-FDA or FUN-1.

7. The method of claim 1, wherein the calibrating curve is generated using different concentrations of the antimicrobial incubated with the reference microbial strain.

8. The method of claim 1, further comprising incubating a separate aliquot of the biological sample with a microbial strain isolated from the patient and the fluorophore, and measuring a second signal of fluorescent intensity of the fluorophore in the microbial strain isolated from the patient in the separate aliquot using flow cytometry.

9. The method of claim 8, wherein the calibrating curve is generated using different concentrations of the antimicrobial incubated with the microbial strain isolated from the patient.

* * * * *